United States Patent [19]

Prochaska et al.

[11] Patent Number: 5,336,685

[45] Date of Patent: Aug. 9, 1994

[54] USE OF FLAVONOIDS TO TREAT MULTIDRUG RESISTANT CANCER CELLS

[75] Inventors: Hans J. Prochaska, New York; Kathleen W. Scotto, Middle Village, both of N.Y.

[73] Assignee: Sloan-Kettering Institute for Cancer Research, New York, N.Y.

[21] Appl. No.: 46,082

[22] Filed: Apr. 12, 1993

[51] Int. Cl.$^5$ ............................................. A61K 31/35
[52] U.S. Cl. ................................................ 514/455
[58] Field of Search ......................................... 514/455

[56] References Cited

U.S. PATENT DOCUMENTS 4,751,224  6/1988  Agarwal et al. ................. 514/248

OTHER PUBLICATIONS

Merchant et al., *Archives of Biochemistry and Biophysics*, vol. 281, No. 1, Aug. 15, 1990, pp. 84–89.
Nebert et al., *Biological Abstracts*, vol. 67, No. 12, abstract No. 74357, 1979.
Deodutta et al., *Biological Abstracts*, vol. 88, No. 8, abstract No. 86703, 1989.
Ziehr et al., *Biological Abstracts*, vol. 91, No. 11, abstract No. 120520, 1991.
Li et al., *Medline Abstracts* No. 84306541, 1984.
Alworth et al., *Medline Abstracts* No. 85177252, 1985.
Ramu, A., et al., Cancer Research 44:4392–4395 (1984).
Twentyman, P. R., et al., Brit. J. Cancer 56(1):55–57 (1987).
Mickley, L. A., et al., J. Bio. Chem. 264:18031–18040 (1989).
Ford, J. M., et al., Pharm. Reviews 42(3):155–199 (1990).
Kadam, S., et al., Cancer Research 52:4735–4740 (1992).
Mizuno, K., et al., Anticancer Research 12:21–26 (1992).

*Primary Examiner*—Marianne M. Cintins
*Assistant Examiner*—William R. A. Jarvis
*Attorney, Agent, or Firm*—John P. White

[57] ABSTRACT

A method of inhibiting the growth of multidrug resistant cancer cells which comprises contacting multidrug resistant cancer cells with an effective amount of a flavonoid compound. Also, a composition for inhibiting the growth of multidrug resistant cancer cells which comprises a physiologically acceptable carrier and an amount of a flavonoid compound.

3 Claims, 14 Drawing Sheets

β-NAPHTHOFLAVONE

α-NAPTHOFLAVONE

FLAVONE 2,3-DIHYDROFLAVONE

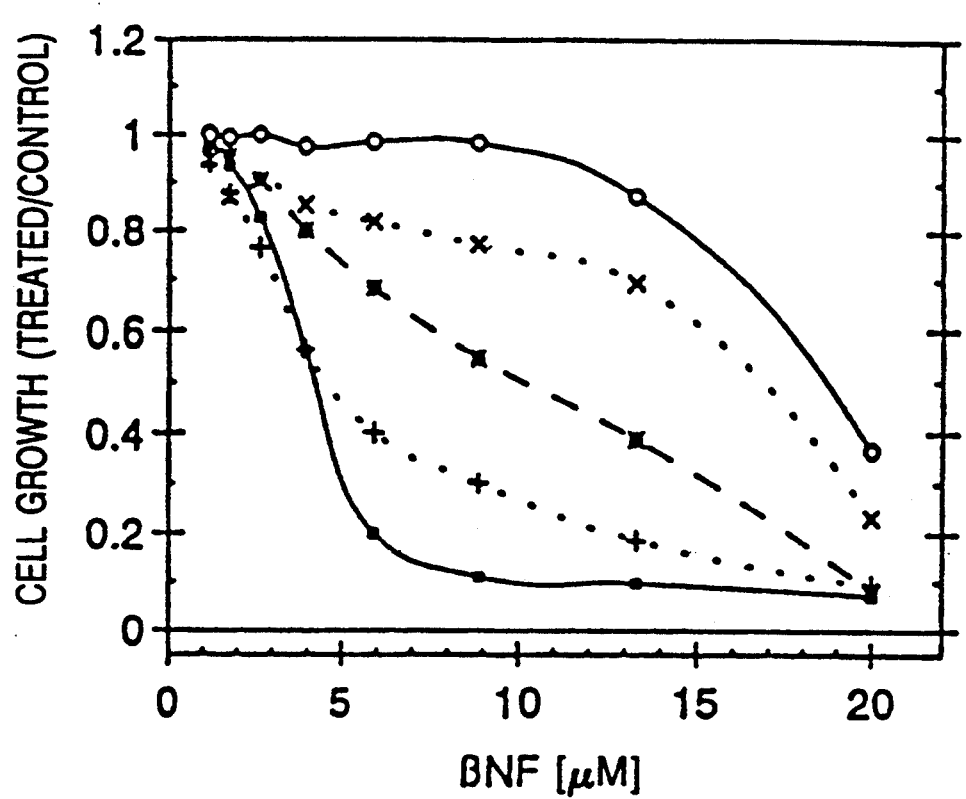

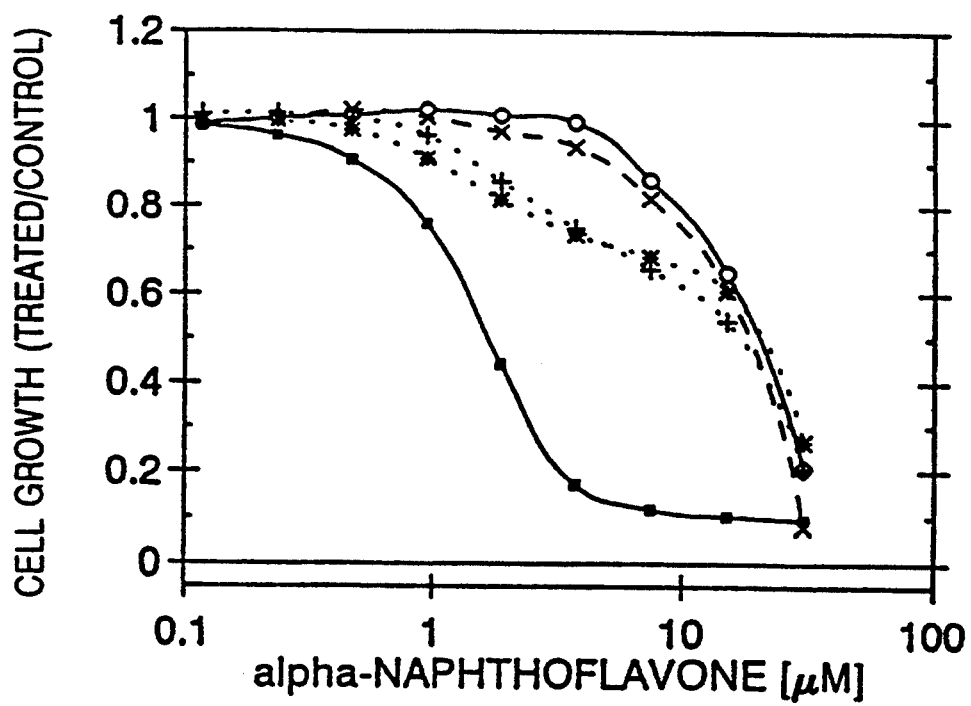

USE OF FLAVONOIDS TO TREAT MULTIDRUG RESISTANT CANCER CELLS

The invention described herein was made in the course of work under Grant No. P01-CA18856-15 from the National Institute of Health. The U.S. Government has certain this invention.

BACKGROUND OF THE INVENTION

Throughout this application, various publications are referenced by Arabic numerals within parentheses. Full citations for these publications may be found at the end of the specification immediately preceding the claims. The disclosures of these publications in their entireties are hereby incorporated by reference into this application in order to more fully describe the state of the art as known to those skilled therein as of the date of the invention described and claimed therein.

A family of compounds, the flavonoids, are selectively toxic to multidrug resistant cells. Several recent studies have linked the regulation of P-glycoprotein (Pgp) gene expression to the expression of the drug-metabolizing P450 genes, with the speculation that, in normal cells, P-glycoprotein may function in conjunction with the P450 enzymes in the detoxication of xenobiotics (34–36). Indeed, benzo[a]pyrene, an inducer and a substrate for cytochrome P450Ia1, is also a substrate for P-glycoprotein (37). While investigating the coordinated regulation of these genes following exposure of multidrug resistant (MDR) cells to inducers of P450 gene expression, it was observed that one of these inducers, β-naphthoflavone (βNF), was considerably more toxic to multidrug resistant cells than to their drug-sensitive counterparts. This collateral sensitivity to βNF and other flavonoid compounds has now been investigated in several multidrug resistant cell lines.

The tendency for cells to develop resistance to chemotherapeutic agents remains a major obstacle to successful cancer treatment. Perhaps the most insidious form of drug resistance has been termed multidrug resistance (MDR), in which cells become cross-resistant to a variety of functionally unrelated chemotherapeutic agents. In laboratory models, this resistance is most often associated with a decrease in drug retention and an overexpression of P-glycoprotein (Pgp), a membrane protein which has been shown to mediate drug efflux (see 1 for review). A direct relationship between P-glycoprotein expression and chemotherapeutic resistance has also been observed in a variety of malignancies (2, 3), including leukemias and lymphomas (4–8), myeloma (9–11), breast cancer (12, 13), ovarian cancer (14) and neuroblastoma (15, 16).

Efforts to overcome multidrug resistance have focused on agents which "reverse" the phenotype by increasing intracellular drug concentrations in resistant cells (17–19). Although these reversal agents have been proposed to act by competing for P-glycoprotein-mediated drug efflux, this has not yet been proven, and the complexity of the multidrug resistant phenotype, as well as the multiple pharmacological activities of many of these agents (20) suggests that other mechanisms may also play a role in the resensitization of multidrug resistant cells (21). Known reversal agents include calcium channel blockers (e.g., verapamil) (22), calmodulin inhibitors (23), indole alkaloids (24), quinolines (25), steroid hormones (26, 27) and immunosuppressive agents (28, 29). Verapamil and cyclosporin A are currently in clinical trial; however, their usefulness is limited by toxic effects (21).

An additional characteristic of some but not all of the multidrug resistant reversal agents is that they can also be selectively toxic to drug-resistant cells in the absence of multidrug resistant drugs. This was first shown for verapamil (30), and has since been observed with other calcium channel blockers, calmodulin inhibitors (31), steroid hormones and nonionic detergents (see 32 for review). The mechanism responsible for this "collateral sensitivity" of multidrug resistant cells has not yet been defined, but, at least in the case of the calcium channel blockers, has been proposed to involve P-glycoprotein (33). However, the selective toxicity of these agents to multidrug resistant cells has not been exploited therapeutically, since the concentration of drug mediating collateral sensitivity is often even higher than that required for reversal (31).

Several flavonoids are up to 15-fold more toxic to multidrug resistant cell lines relative to their parental counterparts. The flavone moiety is critical for selective toxicity to cells possessing the multidrug resistant phenotype, since the closely related congener, 2,3-dihydroflavone, and other complex lipophilic drugs such as tamoxifen or diethylstilbestrol, are largely devoid of this activity. Cells selected for resistance to βNF show a decrease in both P-glycoprotein levels and the multidrug resistant phenotype, as well as a markedly altered morphology. These results suggest that flavonoid compounds may be a useful adjuvant to antineoplastics to prevent the emergence of cells possessing the multidrug resistant phenotype.

SUMMARY OF THE INVENTION

This invention provides a method of inhibiting the growth of multidrug resistant cancer cells which comprises contacting multidrug resistant cancer cells with an effective amount of a flavonoid compound having one of the following possible structures:

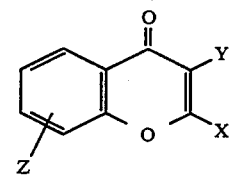

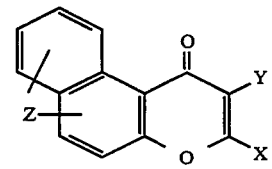

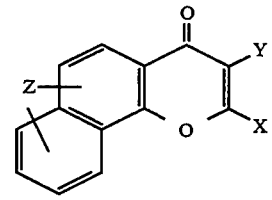

-continued

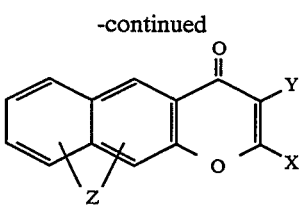

where X can be a phenyl group or a phenyl group substituted with one or two of the following: —OH, —OR, —NH$_2$, —NHR, R being a C$_1$–C$_5$ alkyl group, and where Y can be —H or —OH, and where Z can be —H or —OH, —OR, —NH$_2$, —NHR, R being a C$_1$–C$_5$ alkyl group.

This invention further provides a composition for the inhibition of the growth of multidrug resistant cancer cells comprising a physiologically acceptable carrier and an effective amount of a flavonoid compound having one of the possible structures shown above.

BRIEF DESCRIPTIONS OF THE FIGURES

FIG. 1. Structures of a few of the flavonoid compounds tested for their cytotoxic effects on sensitive and multidrug resistant cell lines.

FIG. 2. Dose-dependent inhibition of cell growth in the parental DC-3F Chinese Hamster lung cell line (o), its Actinomycin D-resistant clones DC-3F/ADII (+), DC-3F/ADIV (*), DC-3F/ADX (■), or by the partial DC-3F/ADX revertant DC-3F/ADXU (x) by ADR (upper frame) and βNF (lower frame). The cells were incubated in microtiter wells with various concentrations of drug for 48 h and assayed for cell growth as described in the "Detailed Description of the Invention."

FIG. 3. Dose-dependent inhibition of cell growth in the parental BE-2C human neuroblastoma cell line (o), its ADR-resistant clones BE-2C/ADR(5) (+) and Act D-resistant subclone, BE-2C/Act(0.2) (*) by ADR (upper frame) and βNF (lower frame). The cells were incubated in microtiter wells with various concentrations of drug for 48 h and assayed for cell growth as described in "Detailed Description of the Invention."

FIG. 4. Photomicrograph of drug-sensitive DC-3F cells (upper left), multidrug resistant DC-3F/ADX cells (upper right) and the βNF-resistant cell lines ADX/ISA12 (lower left), ADX/ISA25 (lower middle), and ADX/ISA50 (lower right). See Detailed Description of the Invention for description of cell lines. Note the altered morphology of the ADX/ISA25 and ADX/ISA50 cells relative to the "parental" DC-3F/ADX cells.

FIG. 5. Dose-dependent inhibition of cell growth in DC-3F cells (o) DC-3F/ADX cells (■) and βNF-resistant clones ADX/ISA12 (*), ADX/ISA25 (x), and ADX/ISA50 (+), by ADR (upper frame), flavone (middle frame), and αNF (lower frame). The cells were incubated in microtiter wells with various concentrations of drug for 48 h and assayed for cell growth as described in Detailed Description of the Invention.

FIG. 6. Western blot analysis of βNF-resistant cell lines. 40 μg total protein from each cell line was examined by Western blot analysis using the C219 antibody, as described in Detailed Description of the Invention. Lane 1, DC-3F/ADX; lane 2, ADX/ISA12; lane 3, ADX/ISA25; lane 4, ADX/ISA50, lane 5, DC-3F.

DETAILED DESCRIPTION OF THE INVENTION

Figure 1A:
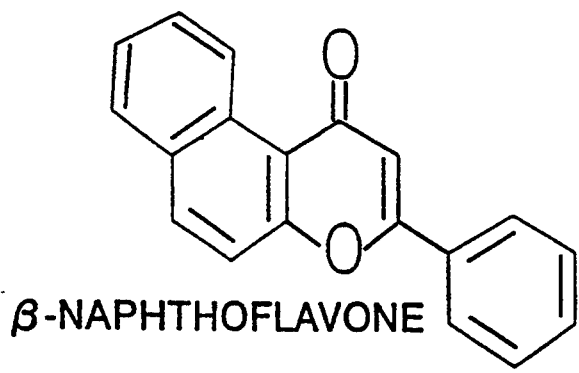
Figure 1B:
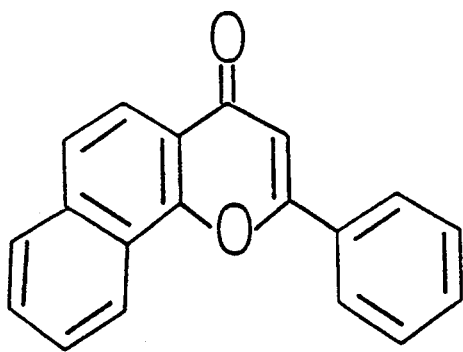
Figure 1C:
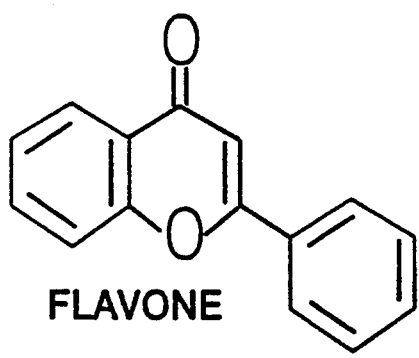
Figure 1D:
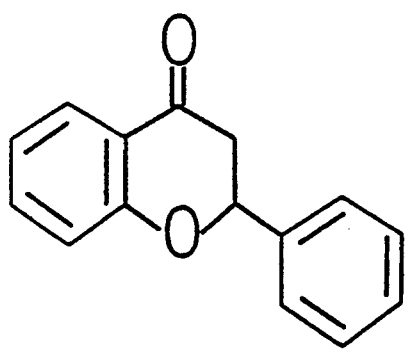

This invention provides a method of inhibiting the growth of multidrug resistant cells which comprises contacting multidrug resistant cells with an amount effective to inhibit the growth of the multidrug resistant cells of a flavonoid compound having the following structure:

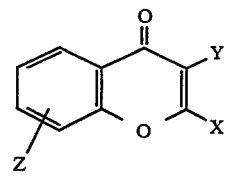

where X can be a phenyl group or a phenyl group substituted with one or two of the following: —OH, —OR, —NH$_2$, —NHR, R being a C$_1$–C$_5$ alkyl group, and where Y can be —H or —OH, and where Z can be —H or —OH, —OR, —NH$_2$, —NHR, R being a C$_1$–C$_5$ alkyl group.

In one embodiment of the invention the flavonoid compound is flavone and the effective concentration is in the range from about 10 μM to about 110 μM. In another embodiment of the invention the flavonoid compound is 3,3',4',7-tetrahydroxyflavone.

This invention also provides a method of inhibiting the growth of multidrug resistant cells which comprises contacting multidrug resistant cells with an amount effective to inhibit the growth of the multidrug resistant cells of a flavonoid compound having the following structure:

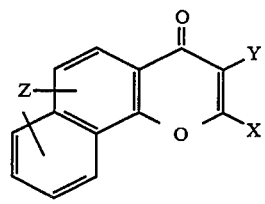

where X can be a phenyl group or a phenyl group substituted with one or two of the following: —OH, —OR, —NH$_2$, —NHR, R being a C$_1$–C$_5$ alkyl group, and where Y can be —H or —OH, and where Z can be —H or —OH, —OR, —NH$_2$, —NHR, R being a C$_1$–C$_5$ alkyl group.

In one embodiment of the invention the flavonoid compound is α-naphthoflavone and the effective concentration is in the range from about 1 μM to about 10 μM.

This invention further provides a method of inhibiting the growth of multidrug resistant cells which comprises contacting multidrug resistant cells with an amount effective to inhibit the growth of the multidrug resistant cells of a flavonoid compound having the following structure:

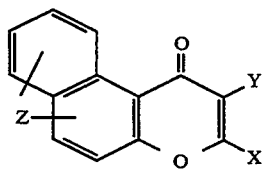

where X can be a phenyl group or a phenyl group substituted with one or two of the following: —OH, —OR, —NH₂, —NHR, R being C₁-C₅ alkyl group, and where Y can be —H or —OH, and where Z can be —H or —OH, —OR, —NH₂, —NHR, R being a C₁-C₅ alkyl group.

In an embodiment of the invention the flavonoid compound is β-naphthoflavone and the effective concentration is in the range from about 1 μM to about 20 μM.

Also provided by this invention is a method of inhibiting the growth of multidrug resistant cells which comprises contacting multidrug resistant cells with an amount effective to inhibit the growth of the multidrug resistant cells of a flavonoid compound having the following structure:

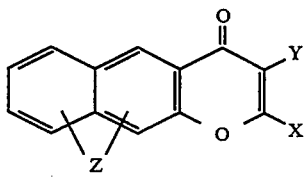

where X can be a phenyl group or a phenyl group substituted with one or two of the following: —OH, —OR, —NH₂, —NHR, R being a C₁-C₅ alkyl group, and where Y can be —H or —OH, and where Z can be —H or —OH, —OR, —NH₂, —NHR, R being a C₁-C₅ alkyl group.

An embodiment of this invention includes y-naphthoflavone as the flavonoid compound.

In an embodiment of this invention, the method of inhibiting the growth of multidrug resistant cells comprises treating multidrug resistant cells. In yet another embodiment of the invention the growth of multidrug resistant cells is inhibited in living organisms.

Methods of determining the effective concentrations are well known in the art. A person of ordinary skill in the art can easily extrapolate the effective concentrations as determined in vitro, and apply it to living organisms to determine the effective concentrations in vivo.

This invention also provides a composition for inhibiting the growth of multidrug resistant cells which comprises a physiologically acceptable carrier and an amount effective to inhibit the growth of multidrug resistant cells of a flavonoid compound having the following structure:

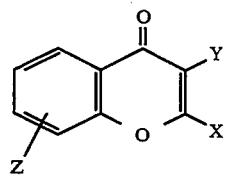

where X can be a phenyl group or a phenyl group substituted with one or two of the following: —OH, —OR, —NH₂, —NHR, R being a C₁-C₅ alkyl group, and where Y can be —H or —OH, and where Z can be —H or —OH, —OR, —NH₂, —NHR, R being a C₁-C₅ alkyl group.

In one embodiment of the invention the flavonoid compound is flavone. In another embodiment of the invention the flavonoid compound is 3,3',4',7-tetrahydroxyflavone.

Additionally provided by this invention is a composition for inhibiting the growth of multidrug resistant cells which comprises a physiologically acceptable carrier and an amount effective to inhibit the growth of multidrug resistant cells of a flavonoid compound having the following structure:

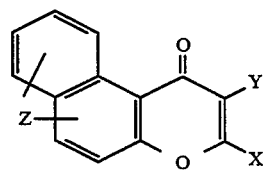

where X can be a phenyl group or a phenyl group substituted with one or two of the following: —OH, —OR, —NH₂, —NHR, R being a C₁-C₅ alkyl group, and where Y can be —H or —OH, and where Z can be —H or —OH, —OR, —NH₂, —NHR, R being a C₁-C₅ alkyl group.

In one embodiment of the invention the flavonoid compound is β-naphthoflavone.

This invention further provides a composition for inhibiting the growth of multidrug resistant cells which comprises a physiologically acceptable carrier and an amount effective to inhibit the growth of multidrug resistant cells of a flavonoid compound having the following structure:

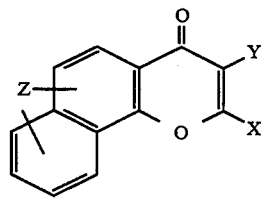

where X can be a phenyl group or a phenyl group substituted with one or two of the following: —OH, —OR, —NH2, —NHR, R being a C₁-C₅ alkyl group, and where Y can be —H or —OH, and where Z can be —H or —OH, —OR, —NH₂, —NHR, R being a C₁-C₅ alkyl group.

In an embodiment of the invention the flavonoid compound is α-naphthoflavone.

This invention also provides a composition for inhibiting the growth of multidrug resistant cells which comprises a physiologically acceptable carrier and an amount effective to inhibit the growth of multidrug resistant cells of a flavonoid compound having the following structure:

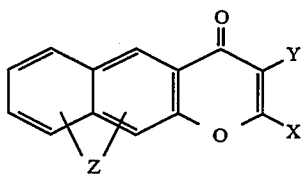

where X can be a phenyl group or a phenyl group substituted with one or two of the following: —OH, —OR, —NH2, —NHR, R being a $C_1$-$C_5$ alkyl group, and where Y can be —H or —OH, and where Z can be —H or —OR, —OR, —NH2, —NHR, R being a $C_1$-$C_5$ alkyl group, In one embodiment of the invention the flavonoid compound is γ-naphthoflavone.

For the purposes of this invention, "physiologically acceptable carrier" means any of the standard pharmaceutical carriers. Examples of suitable carriers are well known in the art and may include, but are not limited to, any of the standard pharmaceutical carriers.

Materials

Actinomycin D (ActD) and ADR were purchased from Sigma (St. Louis, Mo.); vincristine was a generous gift of Eli Lilly (Indianapolis, IN); BNF, α-naphthoflavone (αNF), flavone, 2,3-dihydroflavone (flavanone) (see FIG. 1), verapamil, and tamoxifen were purchased from Aldrich (Milwaukee, Wis.). In order to insure that the effects observed with βNF were not due to impurities, the compound was recrystallized from ethyl acetate. The stock solution of ADR was dissolved in saline, whereas the other compounds were dissolved in spectral-grade DMSO (Fisher, Fair Lawn, N.J.). Tissue culture medium was prepared by the MSKCC media lab, and fetal calf serum was obtained from Hy-Clone (Logan, Utah). Other reagents and other tissue culture supplies were obtained from standard sources via Fisher (Fair Lawn, N.J.).

Treatment of Established Cell Lines

The multidrug resistant sublines of the Chinese hamster lung cell line DC-3F were stepwise selected in increasing concentrations of actinomycin D as described by Bledlet and colleagues (38), and are therefore serially related; DC-3F/ADXU is a revertant of DC-3F/ADX which has been maintained in the absence of actinomycin D for several years. These cells were grown in MEM/F12 with 2 mM glutamine, 100 U/ml penicillin, 100 μg/ml streptomycin, 5% fetal calf serum and the appropriate concentration of actinomycin D (38). The human neuroblastoma cell line, BE-2C, and its multidrug resistant sublines, BE-2C/ADR(5) and BE-2C/Act(0.2) were maintained in the same media, containing 15% fetal calf serum (39).

Cytotoxicity Assays

Cells were maintained in a humidified incubator in 5% $CO_2$ at 37° C. in the absence of selective agent for several days, then seeded in rows 2–12 of a 96-well microtiter plate at 5,000 cells/well in drug-free medium. Following a 24 hour incubation, the medium was decanted and the cells were fed 100 μl/well fresh medium containing 0.1% DMSO. 33.5–100 μl/well of media containing 0.1% DMSO and the appropriate concentration of test compound were then added and thoroughly mixed with the medium in the second row of wells; similar two- to four-fold serial dilutions were then performed in rows 3 through 10 of the microtiter plates. Two rows of cells (rows 11 and 12) were left as untreated controls. The final volume of media in all wells was 100 μl and contained 0.1% final concentration of DMSO. After the cells were allowed to grow for an additional 48 hours, the media was decanted and the plates were submerged in a vat containing 0.2% crystal violet and 2% ethanol for 10 minutes. Plates were then thoroughly rinsed with tap water for 2 minutes, and the retained dye was solubilized by incubation at 45° C. for 90 min with 200 μl/well of 0.5% sodium dodecyl sulfate in 50% ethanol. Plates were then scanned at 610 nm using a microtiter plate reader ($uv_{max}$, Molecular Devices, Palo Alto, Calif.). The amount of retained dye reflects both the cell number and protein content of the well (40).

Selection and Analysis of βNF-resistant DC-3F/ADX Cells

DC-3F/ADX cells were cultured in the absence of actinomycin D for several doubling periods, then selected in the presence of 12.5, 25 and 50 μM βNF. Multiple colonies surviving selection in 12.5 and 25 μM βNF were pooled and designated ADX/ISA12 and ADX/ISA25, respectively. Only one colony survived in 50 μM βNF and was designated ADX/ISA50. βNF-resistant cell lines were maintained in media containing the concentration of βNF used for selection.

Western blot analysis was carried out essentially as described (41). Briefly, 40 μg of total cell protein was electrophoresed on a 7.5% gel, transferred to nitrocellulose and incubated at room temperature for one hour in 5% dry milk/0.1M Tris, pH 7.4. Following blocking, the filter was incubated overnight with 2 μg of C219 antibody in milk solution. Protein-antibody complexes were detected by chemiluminessence, according to the directions of the manufacturer (Amersham, Ill.).

Methods of Calculation and Statistical Treatment of Results

Figure 2A:
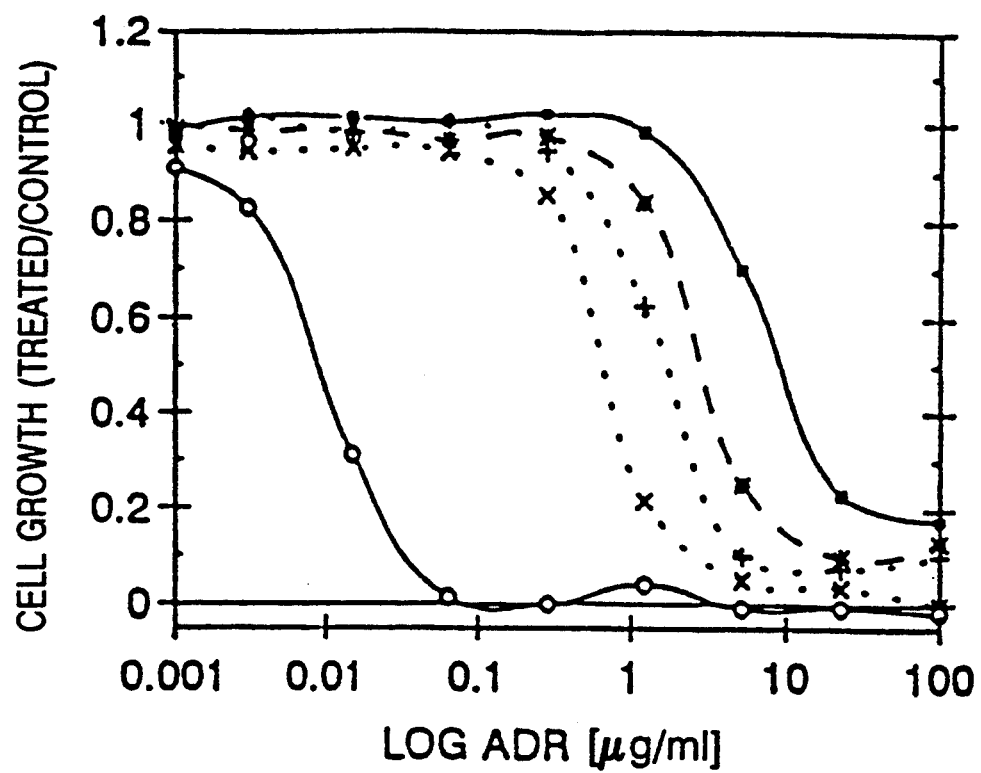

Spectrophotometric data from cytotoxicity studies were imported directly onto formatted spreadsheets using Lotus 1-2-3 software (Cambridge, Mass.). The ratios of the cell masses in drug-treated wells (N=8 wells per concentration) to controls grown on the same plate (N=16) were calculated. The S.E.M. values obtained were generally less than 3% of the mean values. Dose-response curves were then fitted to the data by importing the calculated ratios into the Harvard Graphics software package (Santa Clara, Calif.), from which IC50's could be determined (FIG. 2). The $IC_{50}$±-S.E.M. values given in Table 1 represent the results from three to seven independent experiments analyzed as described above. The statistical significance of the observations were determined by the unpaired t test using the INSTAT software package (GraphPad, San Diego, Calif.).

Results

The results described below are merely examples of the claimed invention and are in no way meant to limit the scope of the invention as claimed.

Typical results demonstrating the dose-dependent inhibition of growth of the Chinese hamster lung cells by βNF and ADR are shown in FIG. 2, and the $IC_{50}$ data obtained from three to seven independent experiments are summarized in Table 1. DC-3F/ADII, DC- 3F/ADIV and DC-3F/ADX all exhibited sensitivity to BNF relative to the parental DC-3F cells, ranging from 3–6-fold (this is a minimum estimate, since the relative insolubility of βNF made it difficult to obtain reliable $IC_{50}$ values for the parent cell line). The sensitivity to βNF roughly correlated with both the concentration of P-glycoprotein and the degree of drug resistance. It is interesting to note that, using the same assay, no potentiation of ADR toxicity in the presence of 1–8 μM βNF was observed (data not shown); therefore, whether flavonoids also act as multidrug resistant reversal agents will require further study.

Figure 3A:
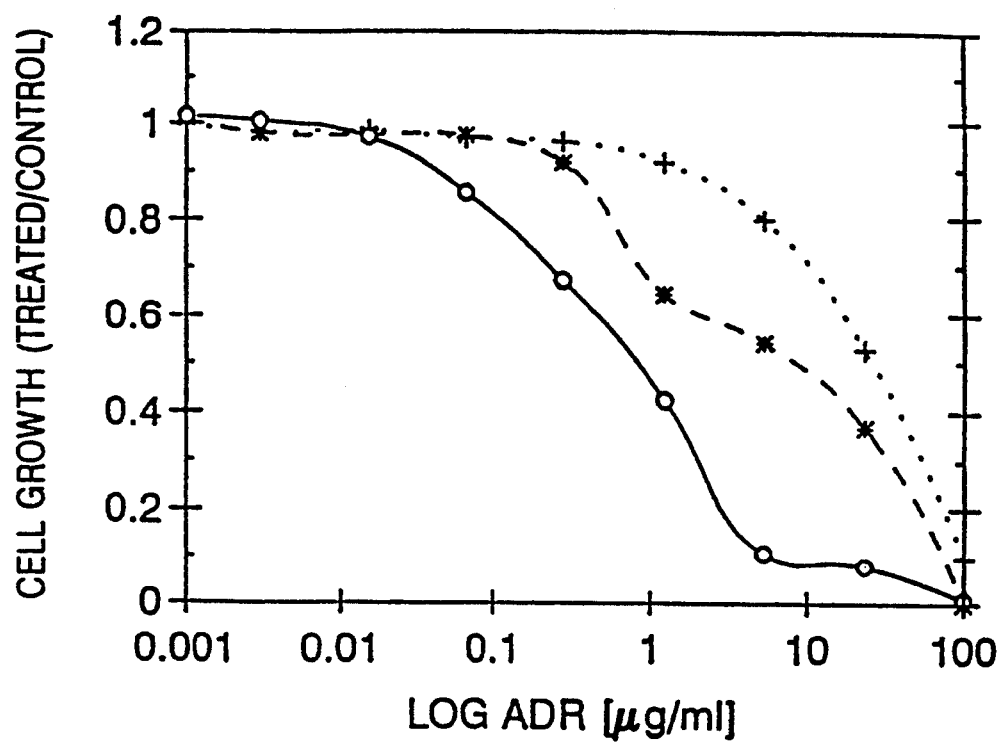
Figure 3B:
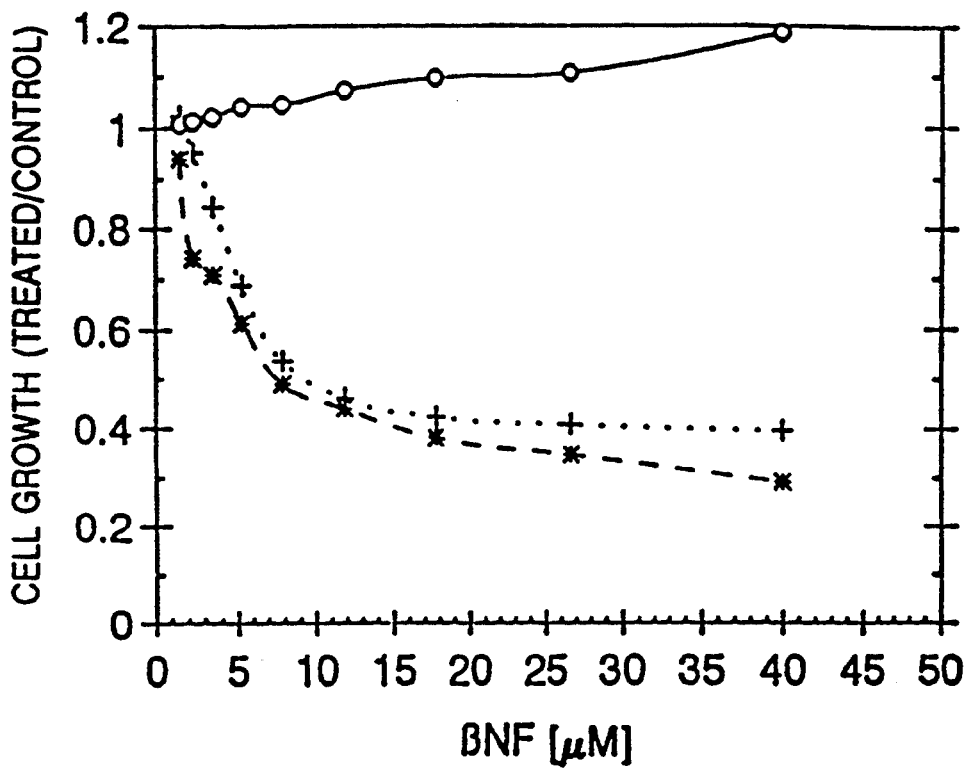
Figure 4A:
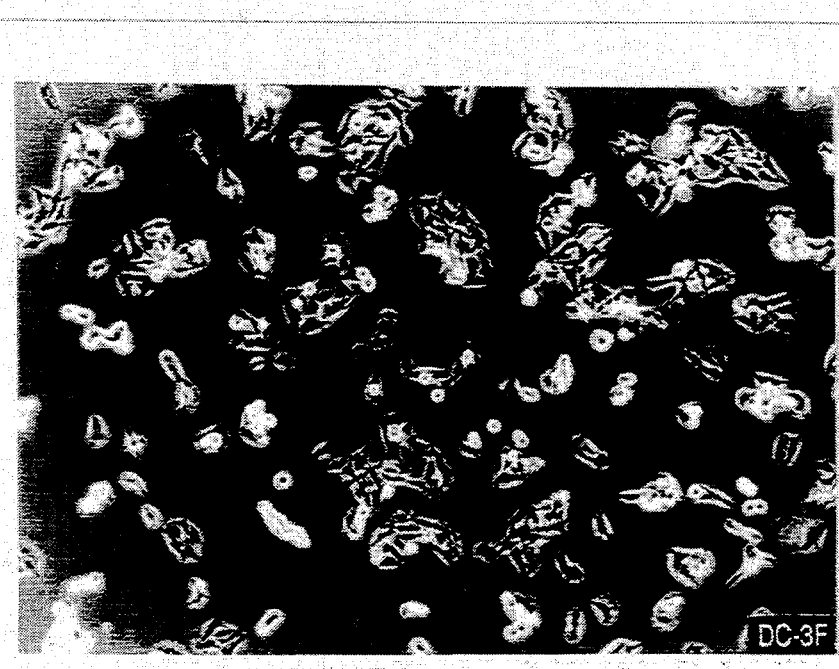
Figure 4B:
Figure 4C:
Figure 4D:
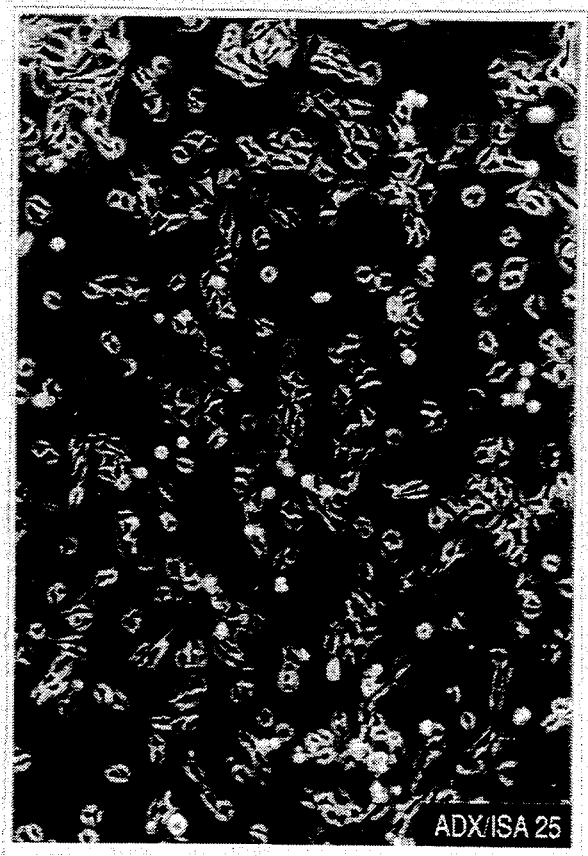
Figure 4E:
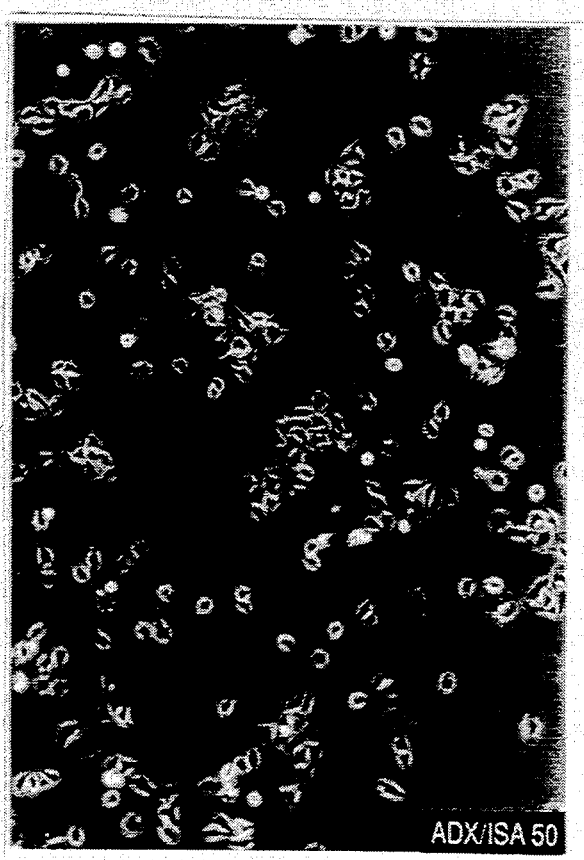

The effect of βNF on human neuroblastoma cell lines selected for resistance to either ADR or actinomycin D (FIG. 3) was investigated to rule out the possibility that collateral sensitivity to flavonoid compounds was species or tissue-specific, or dependent on the drug used for selection of the multidrug resistant phenotype. The multidrug resistant cell lines BE-2C/ADR(5) and particularly BE-2C/ACT(0.2) exhibit a low level of resistance to ADR (27.5 and 8.8-fold relative to the parent BE-2C cells, respectively, as determined by microtiter plate assay), more analogous to what might be observed clinically. When exposed to βNF, the multidrug resistant neuroblastoma cells were much more sensitive than BE-2C cells (an $IC_{50}$ for the parent cells in these experiments was unable to be achieved), confirming the selective toxicity of this compound for the multidrug resistant sublines.

In order to determine whether selective toxicity to the multidrug resistant cells was common to other members of the flavonoid family, the effect of βNF, flavone and 2,3-dihydroflavone (FIG. 1) on DC-3F and DC-3F/ADX cells (Table 2) was investigated. Flavone selectively inhibited the growth of multidrug resistant cells to approximately the same extent as βNF (DC-3F/ADX cells were 4.2-fold more sensitive to this compound than DC-3F cells), while exposure to βNF resulted in an even greater relative toxicity for the multidrug resistant cells (14-fold). The effect of eNF is comparable to that observed for the well-described collateral sensitive agent, verapamil (13.3-fold). It is clear that the flavone structure is important for the selective cytotoxic effects on cells possessing the multidrug resistant phenotype, since the reduction product of flavone (2,3-dihydroflavone) is much less active. Another multidrug resistant reversal agent, the antiestrogen tamoxifen (26), conferred no selective toxicity under these conditions, nor did the highly lipophilic drug, diethylstilbestrol.

Figure 5A:
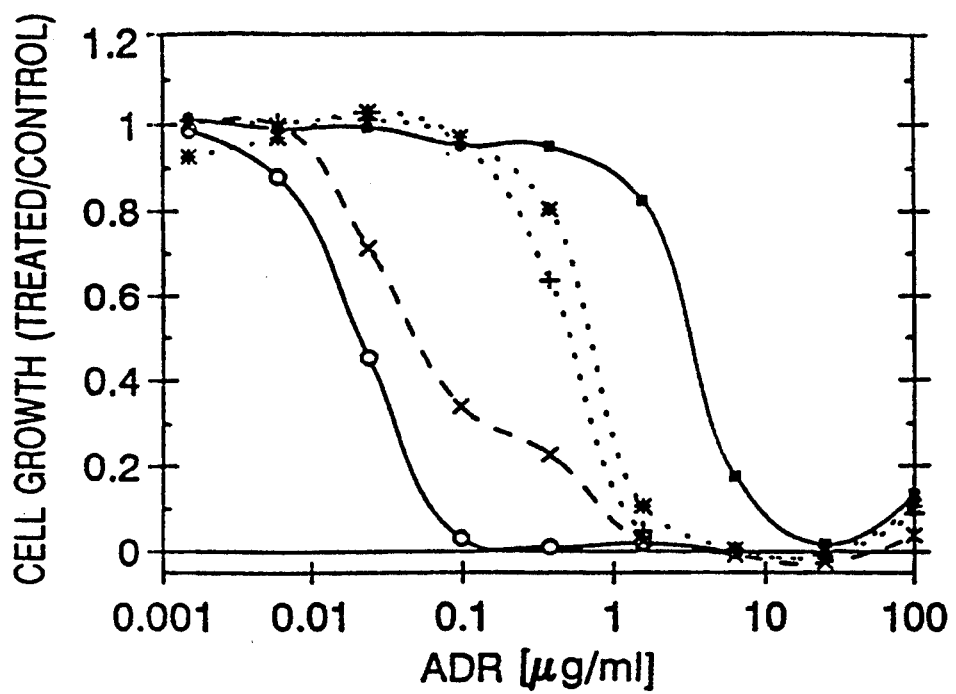
Figure 5B:
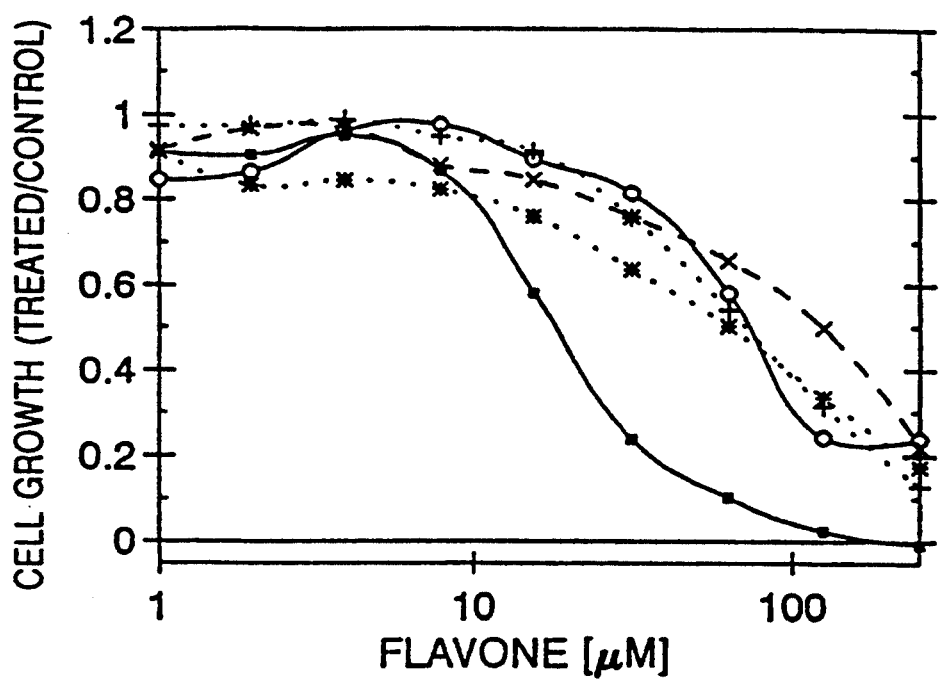
Figure 6:
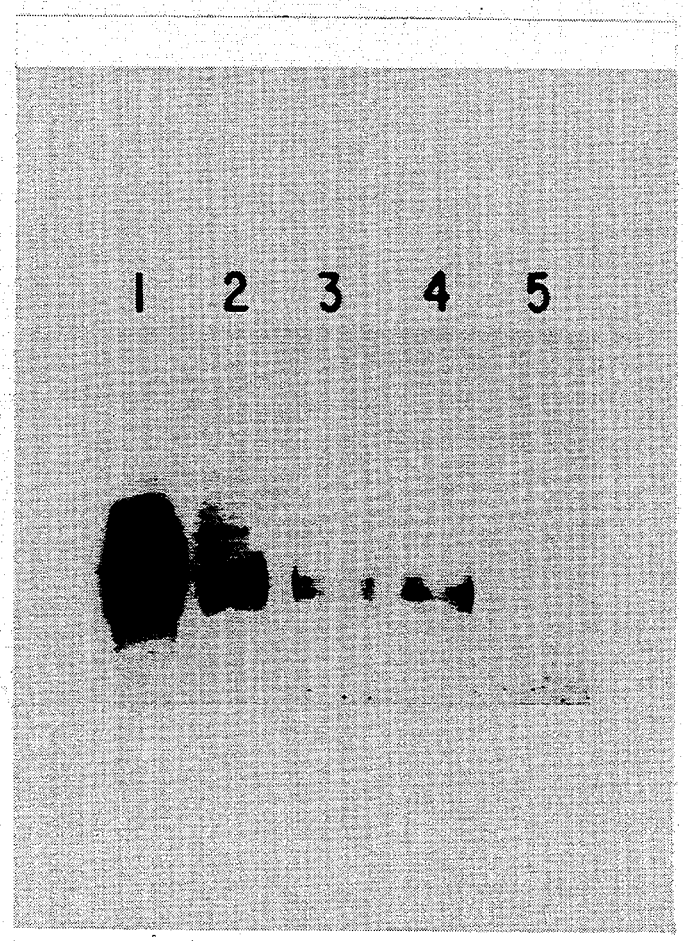

In an initial effort to define the mechanism of action of βNF on multidrug resistant cells, the highly multidrug resistant cell line DC-3F/ADX was selected for "resistance" to the flavonoid ("resistance", as used here, is actually a loss of collateral sensitivity). Three βNF-resistant cell lines, designated ADX/ISA12, ADX/ISA25 and ADX/ISA50, were selected as described in "Detailed Description of the Invention". While ADX/ISA12 was morphologically similar to the DC-3F/ADX cells, ADX/ISA25 and ADX/ISA50 cells possessed a more rounded, less spindle-shaped morphology, reminiscent of the MDR-sensitive DC-3F cell line (FIG. 4). All βNF-resistant cell lines were cross-resistant to flavone and αNF; moreover, these cells partially regained their sensitivity to ADR (5- to 70-fold; see FIG. 5). Western blot analysis (FIG. 6) revealed a dramatic decrease in Pgp levels in the βNF-resistant cell lines (cf. lane 1 rs. lanes 2–4); however these lines have detectable levels of Pgp as compared with the drug-sensitive DC-3F cell line (lane 5).

Discussion

During an investigation into a possible coordinate regulation of P-glycoprotein and P450 gene transcription, a new family of drug resistance modulating compounds, the flavonoids, was identified. These compounds show selective toxicity towards multidrug resistant cells. This selective or "collateral" sensitivity is not specified by the species, tissue of origin, or agent used for selection of the multidrug resistant cells, since toxicity was exhibited by both ADR-selected human neuroblastoma cells and actinomycin D-selected Chinese hamster lung cells. In general, the degree of collateral sensitivity to the compounds studied correlates with both the degree of multidrug resistance as well as the amount of P-glycoprotein present in the cell lines studied. This is particularly apparent in the analysis of the effect of βNF on the serially-related actinomycin D-selected sublines of Chinese hamster DC-3F lung cells (FIG. 2; Table 1), where toxicity of the flavonoids is most pronounced in the highly multidrug-resistant DC-3F/ADX cells, and is markedly decreased in the multidrug resistant revertant cell line, DC-3F/ADXu. An analogous observation has been made using the well-studied resistance modifying agent, verapamil, where the degree of collateral sensitivity increases with increasing multidrug resistance and P-glycoprotein content (33). It is important to note that relative levels of resistance reported here are a minimum estimation since: 1) difficulty with solubility of some compounds, particularly βNF, made it difficult to determine accurate $IC_{50}$ values for parental cells; and 2) the microtiter plate assay, unlike a clonogenic assay, measures survival as a function of cell integrity and adherence, and may underestimate the number of cells destined to die. When multidrug resistant cells were selected for "resistance" to βNF, the most highly resistant cell lines, ADX/ISA25, ADX/ISA50, exhibited a markedly altered morphology relative to their multidrug resistant parent cells, suggesting a less differentiated state. This is particularly intriguing in light of early studies of Biedler and colleagues (42) who showed that when the morphologically undifferentiated, tumorigenic DC-3F cells were selected for multidrug resistance, they assumed a more differentiated morphology and a decreased tumorigenicity (referred to as a "reverse transformation" phenotype). More recent studies have also indicated a relationship between P-glycoprotein expression and state of differentiation (39, 43), although the extent and significance of this relationship is still unclear. It is interesting to note that, while the expression of P-glycoprotein is within two-fold in all three βNF-resistant cell lines, only ADX/ISA25 and ADX/ISA50 cells exhibit a morphological change. While changes in morphology alone are not necessarily indicative of a change in the state of differentiation, it suggests that the changes in morphology are a result of an event distinct from or in addition to the decrease in P-glycoprotein concentration in these cells. Flavonoids are naturally-occurring compounds found in many edible plants (it has been estimated that the average American consumes as much as 1 gram of flavonoids/day [44]). Moreover, compounds such as βNF are regarded as non-carcinogenic and relatively non-toxic and can prevent the development of carcinogen-induced tumors (see 44 for review). Although decreased amounts of P-glycoprotein may be a secondary and not a causal mechanism to survive exposure to βNF by multidrug resistant cells, the clinically relevant point is that multidrug resistant cells that tolerate βNF partially regain sensitivity to antineoplastic drugs such as ADR. Thus, one could envision a chemotherapeutic regimen wherein a flavonoid would be administered between cycles of chemotherapy, to prevent the proliferation of multidrug resistant tumor cells.

TABLE 1

Effect of Adriamycin ® (ADR) and β-naphthoflavone (βNF) on the growth of sensitive and Actinomycin D-resistant Chinese hamster lung cells

| | ADR | | |
|---|---|---|---|
| Cell Line | IC$_{50}$ [μg/ml] | p | Fold-Resistance |
| DC-3F | 0.036$^a$ ± 0.020$^b$ | — | 1.0 |
| DC-3F/ADII | 2.1 ± 0 2 | 0.001 | 58 |
| DC-3F/ADIV | 4.2 ± 0.9 | 0.011 | 120 |
| DC-3F/ADX | 11 ± 2 | 0.0093 | 310 |
| DC-3F/ADXU | 1.3 ± 0.4 | 0.026 | 36 |

| | β-naphthoflavone | | |
|---|---|---|---|
| Cell Line | IC50 [μM] | p | Fold-Sensitivity |
| DC-3F | 16$^c$ ± 0.5 | — | 1.0 |
| DC-3F/ADII | 4.8 ± .5 | <0.0001 | 3.2 |
| DC-3F/ADIV | 5.4 ± 1.0 | 0.0015 | 2.9 |
| DC-3F/ADX | 2.7 ± 1.0 | <0.0001 | 5.7 |
| DC-3F/ADXU | 13.3 ± 1.8 | 0.70 | 1.2 |

$^a$Determinations made from cells exposed to ADR in microtiter plates grown in parallel with βNF-treated plates. The fold-resistance values are similar to those previously reported (N = 3 experiments for each cell line).
$^b$Mean ± S.E.M.
$^c$The IC$_{50}$ was difficult to determine in parental cells (DC-3F) due to the tendency of the βNF to precipitate at concentrations greater than 20–30 μM. In 5 of 7 experiments, the IC$_{50}$ ranged between 30 to 100 μM. The mean shown represents the IC$_{50}$'s for two experiments where solubility was not a factor in determining the value. Thus, it is likely that the value shown overestimates the toxicity of βNF in drug-sensitive cells. N = 7 independent experiments for the remaining cell lines except for ADXU (N = 3 experiments).

TABLE 2

Effects of other flavones on the growth of parental (DC-3F) and Antinomycin D-resistant (DC-3F/ADX) cell lines. Treatment of cells and methods for analyses are given in Detailed Description of the Invention.

| | IC$_{50}$ [μM] | | Fold- |
|---|---|---|---|
| Compound | DC-3F | DC-3F/ADX | Sensitivity |
| Flavonoid | | | |
| β-naphthoflavone | 13 | 3.1 | 4.2 |
| α-naphthoflavone | 15 | 1.1 | 14.0 |
| Flavone | 58 | 14 | 4.1 |
| 2,3-Dihydroflavone | 60 | 52 | 1.2 |
| Non-flavonoid | | | |
| verapamil | 60 | 4.5 | 13.3 |
| tamoxifen | 4 | 3.1 | 1.3 |
| diethylstilbestrol | 5.3 | 5.3 | 1.0 |

REFERENCES

1. Chin, K. -V., Pastan, I., and Gottesman, M. M. Function and regulation of the human multidrug resistance gene. Advances in Cancer Res., 60:157–180, 1993.
2. Cordon-Cardo, C. and O'Brien, J. P. The Multidrug Resistance Phenotype in Human cancer. In DeVita, V. T., Hellman, S. and Rosenberg, S. A. (eds). Important Advances in Oncology. 1991. Lippencott and Co., New York.
3. Goldstein, L. J., Pastan, I. and Gottesman, M. M. Multidrug-resistance in human cancer. Critical reviews in Oncology/Hematology, 12:243–253, 1992.
4. Sato, H., Preisler, H., Day, R., Raza, A., Larson, R., Browman, G., Goldberg, J., Vogler, R., Grunwald, H., Gottlieb, A., Bennett, J., Gottesman, M., and Pastan, I. MDR1 transcript levels as an indication of resistant disease in acute myelogenous leukaemia. Br. J. Haematol., 75:340, 1990.
5. Kuwazuru, Y., Yoshimura, A., Hanada, S., Utsunomiya, A., Makino, T., Ishibashi, K., Kodama, M., Iwahashi, M., Arima, T., and Akiyama, S. I. Expression of the multidrug transporter, P-glycoprotein, in acute leukemia cells and correlation to clinical drug resistance. Cancer, 66:868 1990.
6. Pirker, R., Wallnet, J., Geissler, K., Linkesch, W., Haas, O. A., Bettelheim, P., Hopfner, M., Scherrer, R., Valent, P., Havelec, L., Ludwig, H., and Lechner, K. MDR1 gene expression and treatment outcome in acute myeloid leukemia. J. Natl. Cancer Inst., 83:663, 1991.
7. Marie, J. P., Zittoun, R., and Sikic, B. I. Multidrug resistance (mdr1) gene expression in adult acute leukemias: correlations with treatment outcome and in vitro drug sensitivity. Blood, 78:586, 1991.
8. Campos, L., Guyotat, D., Archimbaud, E., et al. Clinical significance of multidrug resistance P-glycoprotein expression on acute non-lymphoblastic leukemia cells at diagnosis. Blood, 79:473–476, 1992.
9. Salmon, S., Grogan, T. M., Miller, T. Scheper, R., and Dalton, W. S. Prediction of doxorubicin resistance in vitro in myeloma, lymphoma, and breast cancer by P-glycoprotein staining. J. Natl. Cancer Inst., 81:696, 1989.
10. Epstein, J., Xiao, H., and Oba, B. K. P-glycoprotein expression in plasma-cell myeloma is associated with resistance to VAD. Blood, 74:913–917, 1989.
11. Dalton, W. S., Grogan, T. M., Meltzer, P. S., Scheper, R. J., Durie, B. G. M., et al. Drug-resistance in multiple myeloma and non-Hodgkin's lymphoma: detection of P-glycoprotein and potential circumvention by addition of verapamil to chemotherapy. J. Clin. Oncol., 7:415–424, 1989.
12. Ro, J., Sahin, A., Ro, J. Y., et al. Immunohistochemical analysis of P-glycoprotein expression correlated with chemotherapy resistance in locally advanced breast cancer. Hum. Pathol., 21:787–791, 1990.
13. Verrelle, P., Meissonnier, F., Fonck, Y., et al. Clinical relevance of immunohistochemical detection of multidrug resistance P-glycoprotein in breast carcinoma. J. Natl. Cancer Inst., 83:111–116, 1991.
14. Holzmayer, T. A., Hilsenbeck, S., Von Hoff, D. D., et al. Clinical correlates of MDR1 (P-glycoprotein) gene expression in ovarian and small-cell lung carcinomas. J. Natl. Cancer Inst., 84:1486–1491, 1992.
15. Goldstein, L. J., Fogo, A. T., Ueda, K., Crist, W., Green, A., Brodeur, G., Pastan, I., and Gottesman, M. Expression of the multidrug resistance, MDR1, gene in neuroblastomas. J. Clin. Oncol., 8:128, 1990.
16. Bourhis, J., Benard, J., Hartmann, O, Boccon-Gibod, L., Lemerle, J., and Riou, G. Correlation of MDR1 gene expression with chemotherapy in neuroblastoma. J. Natl. Cancer Inst., 81:1401, 1989.
17. Twentyman, P. R. MDR1 (P-glycoprotein) gene expression - implications for resistance modifier trials. J. Natl. Cancer Inst., 84(19):1458–1460, 1992.
18. Ford, J. M., and Halt, W. N. Pharmacology of drugs that alter multidrug resistance in cancer. Pharmacol. Rev., 42:155–199, 1990.

19. Stewart, D. J., and Evans, W. K. Non-chemotherapeutic agents that potentiate chemotherapy efficacy. Cancer Treat. Rev., 16:1–40, 1989.
20. Schwartz, A., and Triggle, D. J. Cellular action of calcium channel blocking drugs. Ann. Rev. Med., 35:325–329, 1984.
21. Murren, J. R., and Halt, W. N. Commentary: Why haven't we cured multidrug resistant tumors? Oncology Res., 4(1):1–6, 1992.
22. Tsuruo, T., Iida, H., Tsukagoshi, S. and Sakurai, Y. Overcoming of vincristine and adriamycin induced cytotoxicity by verapamil in P388 leukemia in vivo and in vitro through enhanced cytotoxicity of vincristine by verapamil. Cancer Res. 41:1967–1972, 1981.
23. Tsuruo, T., Iida, H., Tsukagoshi, S. and Sakurai, Y. Increased accumulation of vincristine and adriamycin in drug-resistant P388 tumor cells following incubation with calcium antagonists and calmodulin inhibitors. Cancer Res. 43:2905–2910, 1982.
24. Kadam, S., Maus, M. Poddig, J., Schmidt, S., Rasmussen, R., Novosad, E., Plattnet, J., and McAlpine, J. Reversal of multidrug resistance by two novel indole derivatives. Cancer Res., 52:4735–4740, 1992.
25. Tsuruo, T., Iida, H., Kitatani, Y., Yokoto, K., Tsukagoshi, S., and Sukurai, Y. Effect of quinidine and related compounds on cytotoxicity and cellular accumulation of vincristine and Adriamycin in drug-resistant tumor cells. Cancer Res., 44:144–148, 1984.
26. Stuart, N. S. A., Philip, P., Harris, A. L., Tonkin, K., Houlbrook, S., Kirk, J., Lien, E. A., and Carmichael, J. High-dose tamoxifen as an enhancer of etoposide cytotoxicity. Clinical effects and in vitro assessment in p-glycoprotein expressing cell lines. 833–839, 1992.
27. Ramu, A., Glaubiger, D. and Fuks, Z. Reversal of acquired resistance to doxorubicin in P388 murine leukemia cells by tamoxifen and other triparanol analogues. Cancer Res. 44:4392–4395, 1984.
28. Twentyman, P. R., Fox, N. E., and White, D. J. G. Cyclosporine A and its analogues as modifiers of Adriamycin and vincristine resistance in a multidrug resistant human lung cancer cell line. Br. J. Cancer, 56:55–60, 1987.
29. Mizuno, K., Furuhashi, Y., Misawa, T. Iwata, M., Kawai, M., Kikkawa, F., Kano, T., and Tomoda, Y. Modulation of multidrug resistance by immunosuppressive agents: cyclosporin analogues, FK506 and mizoribine- Anticancer Res., 12:21–26, 1992.
30. Wart, J. R., Brewer, F., Andersen, M. and Fergusson, J. Verapamil hypersensitivity of vincristine-resistant Chinese hamster ovary cells. Cell Biol. Int. Rep. 10:389–399, 1986.
31. Schuurhuis, G. J., Pinedo, H. M., Broxterman, H. J., van Kalken, C. K., Kuiper, C. M., and Lankelma, J. Differential sensitivity of multi-drug-resistant and -sensitive cells to resistance-modifying agents and the relation with reversal of anthracycline resistance. Int. J. Cancer, 46:330–336, 1990.
32. Cano-Gauci, D. F. and Riordan, J. R. Collateral sensitivity of multidrug-resistant cells. in Molecular and Cellular Biology of Multidrug Resistance in Tumor Cells. Roninson, I. (ed.) Plenum Press, New York, 1991.
33. Spengler, B. A., Druskin, H., Safa, A., Meyers, M. B. and Biedler. Rapid loss of resistance and P-glycoprotein expression in multidrug-resistant cells treated with verapamil. Proc. Am. Assoc Cancer Res. Abst#2237, 1991.
34. Cowan, K. H., Batist, G., Tulpule, A., Sinha, B. K., and Meyers, C. E. Similar biochemical changes associated with multidrug resistance in human breast cancer cells and carcinogen-induced resistance to xenobiotics in rats. Proc. Natl. Acad. Sci. USA, 83:9328–9332, 1986.
35. Fairchild, C. R., Ivy, S. P., Rushmore, T., Rushmore, G., Lee, G., Kuo, P., Goldsmith, M. E., Meyers, C. E., Farbet, E., and Cowan, K. Carcinogen-induced mdr overexpression is associated with xenobiotic resistance in rat preneoplastic liver nodules and hepatocellular carcinomas. Proc. Natl. Acad. Sci. USA, 84:7701–7705, 1987.
36. Burr, R. K., and Thorgeirsson, S. S. Coinduction of MDR1 multidrug resistance and cytochrome P-450 genes in rat liver by xenobiotics. J. Natl. Cancer Inst., 80:1383–1386, 1988.
37. Yeh, G. C., Lopaczynska, J., Poore, C. M. and Phang, J. P. new functional role for P-glycoprotein: Efflux pump for benzo(a)pyrene in human breast cancer MCF-7 cells. Cancer Res. 20:6692–6695, 1992.
38. Biedler, J. L., and Reihm, H. Cellular resistance to actinomycin D in Chinese hamster lung cells in vitro: cross resistance, radioautographic and cytogenetic studies. Cancer Res., 30:1174–1184, 1970.
39. Biedler, J. L., Casals, D., Chang, T-d., Meyers, M., Spengler, B. A. and Ross, R. A. Multidrug-resistant human neuroblastoma cells are more differentiated than controls and retinoic acid further induces lineage-specific differentiation- Advances in Neuroblastoma Research 3. Evans, A. E., D'Angio, G. J., Knudson, A. G., Jr., and Seeger, R. C. (eds.) Wiley-Liss, New York, 1991.
40. Prochaska, H. P. and Santamaria, A. B. Direct measurement of NAD(P)H:quinone reductase from cells cultured in microtiter wells: A screening assay for anticarcinogenic enzyme inducers. Anal. Biochem. 169:328–336, 1988.
41. Meyers, M. B., Rittmann-Grauer, L., O'Brien, J. P., and Sara, A. R. Characterization of monoclonal antibodies recognizing a $M_r$ 180,000 P-glycoprotein: differential expression of the $M_r$ 180,000 and $M_r$ 170,000 P-glycoproteins in multidrug-resistant human tumor cells. Cancer Res., 49:3209–3214, 1989.
42. Biedler, J. L, Riehm, H., Peterson, R. H. F. and Spengler, B. A. Membrane-mediated drug resistance and phenotypic reversion to normal growth behavior of Chinese hamster lung cells. J. Natl Cancer Inst. 55:671–677, 1975.
43. Mickley, L. A., Bates, S. E., Richert, N. D., Currier, S., Tanaka, S., Foss, F., Rosen, N., Fojo, A. Modulation of 2O the expression of a multidrug-resistance gene (MDR1/Pgp) by differentiating agents. J. Biol Chem. 264:18031–18040, 1989.
44. McKillop, D., and Case, D. E. Commentary. Mutagenicity, carcinogenicity and toxicity of β-naphthoflavone, a potent inducer of P448. Biochemical Pharmacology, 41(1):1–7, 1991.

What is claimed is:

1. A method of inhibiting the growth of multidrug resistant cells comprising contacting said multidrug resistant cells with an amount effective to inhibit the growth of multidrug resistant cells of a flavonoid compound having the following structure:

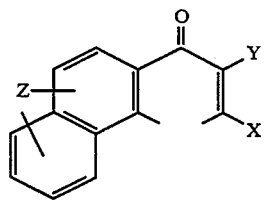

wherein X is a phenyl group or is a phenyl group substituted with one or more of the following: —OH, —OR, —NH$_2$, —NHR, R being a C$_1$–C$_5$ alkyl group, and wherein Y is —H or —OH, and wherein Z is —H or —OH, —OR, —NH$_2$, —NHR, R being a C$_1$–C$_5$ alkyl group.

2. The method of claim 1, wherein the flavonoid compound is α-naphthoflavone.

3. The method of claim 2, wherein the effective concentration is in the range from about 1 μM to about 10 μM.

* * * * *